United States Patent
Golan et al.

(10) Patent No.: US 10,215,711 B2
(45) Date of Patent: Feb. 26, 2019

(54) DETERMINING OXIDATION OF PHOTOCONDUCTOR MEMBERS BASED ON OBTAINED SPECTRUM FROM OPTICAL SPECTROSCOPY

(71) Applicant: HP INDIGO B.V., Amstelveen (NL)

(72) Inventors: Eviatar Golan, Ness Ziona (IL); Fernanda Orlik, Yavne (IL); Mirit Shitrit, Ness Ziona (IL); Sasi Moalem, Ness Ziona (IL); Reut Diamant, Ness Ziona (IL)

(73) Assignee: HP INDIGO B.V., Amstelveen (NL)

(*) Notice: Subject to any disclaimer, the term of this patent is extended or adjusted under 35 U.S.C. 154(b) by 97 days.

(21) Appl. No.: 15/521,813

(22) PCT Filed: Jan. 16, 2015

(86) PCT No.: PCT/EP2015/050771
§ 371 (c)(1),
(2) Date: Apr. 25, 2017

(87) PCT Pub. No.: WO2016/112991
PCT Pub. Date: Jul. 21, 2016

(65) Prior Publication Data
US 2017/0248527 A1    Aug. 31, 2017

(51) Int. Cl.
*G03G 15/04*    (2006.01)
*G01N 21/95*    (2006.01)
(Continued)

(52) U.S. Cl.
CPC .............. *G01N 21/95* (2013.01); *B08B 3/08* (2013.01); *G01N 21/3563* (2013.01);
(Continued)

(58) Field of Classification Search
CPC .... G01N 21/3563; G01N 21/65; G01N 21/95; G03G 15/04; G03G 15/553; G03G 15/75; G03G 15/5033
(Continued)

(56) References Cited

U.S. PATENT DOCUMENTS 6,818,894 B2 * 11/2004 Takoudis ........... G01N 21/3563
                                                      250/336.1
7,620,343 B2   11/2009 Miyaji et al.
(Continued)

FOREIGN PATENT DOCUMENTS

| JP | 2001330977 | 11/2001 |
| JP | 2015007753 | 1/2015 |
| WO | WO-2011081079 | 7/2011 |

OTHER PUBLICATIONS

Alvarez-Macias, C. et al. "Influence of light-soaking treatment on the optoelectronic properties of polymorphous silicon thin films to be used in solar cells", 2013 IEEE 39th Photovoltaic Specialists Conference (PVSC), IEEE, Jun. 16, 2013, pp. 526-529.
(Continued)

*Primary Examiner* — Que Tan Le
(74) *Attorney, Agent, or Firm* — HP Inc. Patent Department (57) ABSTRACT

A method is described in which a spectrum of a surface of a photoconductor member is obtained using optical spectroscopy; and an extent of oxidation of the surface is determined based on the obtained spectrum.

15 Claims, 4 Drawing Sheets

(51) Int. Cl.
*G01N 21/3563* (2014.01)
*G01N 21/65* (2006.01)
*G03G 15/00* (2006.01)
*G03G 21/00* (2006.01)
*B08B 3/08* (2006.01)
*G01N 21/552* (2014.01)
*G01N 21/35* (2014.01)

(52) U.S. Cl.
CPC ........... *G01N 21/552* (2013.01); *G01N 21/65* (2013.01); *G03G 15/04* (2013.01); *G03G 15/5033* (2013.01); *G03G 15/553* (2013.01); *G03G 15/75* (2013.01); *G03G 21/0005* (2013.01); *G01N 2021/3568* (2013.01); *G01N 2021/3595* (2013.01); *G01N 2201/12* (2013.01); *G03G 21/0094* (2013.01)

(58) Field of Classification Search
USPC .............................................. 250/559.4, 221
See application file for complete search history.

(56) References Cited

U.S. PATENT DOCUMENTS

| | | |
|---|---|---|
| 7,773,933 B2 | 8/2010 | Ishino et al. |
| 8,180,271 B2 | 5/2012 | Hatakeyama et al. |
| 8,750,760 B2 | 6/2014 | Shu |
| 2002/0127326 A1 | 9/2002 | Boukherroub et al. |

OTHER PUBLICATIONS

Gleskova, H. et al. "Properties of Au/SiO2/a-Si:H solar cells with wet oxide", Materials Letters, North Holland Publishing Company, Amsterdam, NL, vol. 16, No. 6, Jun. 1993, pp. 305-308.

Hersam, M.C., et al. "Atomic-level study of the robustness of the Si(100)-21:H surface following exposure to ambient conditions", Applied Physics Letters, American Institute of Physics, vol. 78, No. 7, Feb. 12, 2001, pp. 886-888.

Vinod, P. N. et al. "Surface and optical characterization of the porous silicon textured surface", Journal of Materials Science: Materials in Electronics, Kluwer Academic Publishers, BO, vol. 16, No. 1, 2005, pp. 1-6.

* cited by examiner

DETERMINING OXIDATION OF PHOTOCONDUCTOR MEMBERS BASED ON OBTAINED SPECTRUM FROM OPTICAL SPECTROSCOPY

CROSS-REFERENCE TO RELATED APPLICATIONS

This application is a U.S. National Stage Application of and claims priority to International Patent Application No. PCT/EP2015/050771, filed on Jan. 16, 2015, and entitled "DETERMINING OXIDATION OF PHOTOCONDUCTOR MEMBERS."

BACKGROUND

In some examples of digital printers and printing presses an image of the page to be printed is projected by a light source onto a photoconductor member, so that areas not exposed to the light become electrostatically charged. In some examples of printers, i.e. examples which use toner, the charged areas attract toner particles. In other examples of printers, i.e. examples which use liquid ink, the charged areas remain clean while discharged areas (e.g. areas discharged by the light source) attract the liquid ink.

BRIEF DESCRIPTION OF THE DRAWINGS

For a better understanding of the examples described herein, and to show more clearly how the examples may be carried into effect, reference will now be made, by way of example only, to the following drawings in which.

DETAILED DESCRIPTION

The surface of a photoconductor member maintains a high electrical resistivity to hold electrostatic charges in place and prevent charge drifting. Oxidation of the surface of a photoconductor member can increase its lateral conductivity, which can lead to a reduction of print quality.

Oxidation of a surface can be detected and measured using techniques such as energy dispersive x-ray spectroscopy (EDS) and x-ray photoelectron spectroscopy (XPS). However, these techniques may be destructive and therefore may not be suitable to be used to check the condition of a photoconductor member during the printing process.

A process of checking the condition of a photoconductor member may comprise, for example, a series of steps which include obtaining a spectrum of a surface of a photoconductor member, and determining an extent of oxidation of the surface based on the obtained spectrum. Other steps and procedures may also be used with these steps for checking the condition of a photoconductor member.

The examples described herein refer to optical spectroscopy and optical spectrometers. As used herein, the term optical spectroscopy is intended to encompass spectroscopy techniques which measure how a material interacts with light, which may be visible, ultraviolet or infrared light. The term optical spectrometer is intended to denote an apparatus to implement an optical spectroscopy technique.

Figure 1:
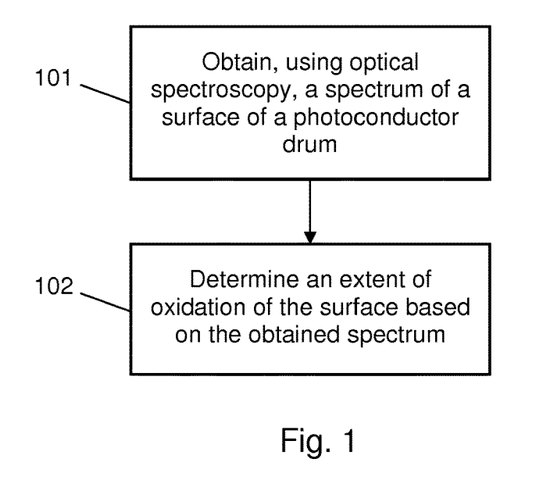
FIG. 1 is a flowchart of an example of a method of determining an extent of oxidation of a surface of a photoconductor.

FIG. 1 shows an example of a method. The method comprises obtaining, using optical spectroscopy, a spectrum of a surface of a photoconductor member, block 101. The photoconductor member may comprise, for example, a photoconductor drum, a photoconductor belt, or any other form of photoconductor unit to be used in a printing apparatus. In some examples the method comprises using Fourier Transform Infrared, FTIR, spectroscopy to obtain the spectrum. In some examples the method comprises using Raman spectroscopy to obtain the spectrum. In some examples block 101 is performed on a photoconductor member which is separate from a printing apparatus e.g. in a maintenance module. In some examples block 101 is performed on a photoconductor member which is installed in a printing apparatus.

In block 102, an extent of oxidation of the surface is determined based on the obtained spectrum. In some examples the photoconductor member comprises multiple layers of photoconductor material. In some examples the surface of the photoconductor member comprises an outer protective layer and at least one inner layer. In some examples block 102 comprises determining how many layers of photoconductor material are oxidised. In some examples in which the photoconductor member comprises multiple layers, block 102 comprises determining an extent of oxidation of each layer comprised in the photoconductor member.

In some examples the determined extent of oxidation comprises a numerical amount, such as a percentage, of an oxidation product of a material comprised in the photoconductor member. In some such examples the numerical amount indicates the amount of the oxidation product comprised in the photoconductor member. In some examples the determined extent of oxidation comprises a numerical amount of a component of an oxidation product of a material comprised in the photoconductor member.

In one example in which the photoconductor member comprises amorphous silicon, the outer protective layer comprises the molecules Si—H and Si—C. Oxidation of the photoconductor material causes Si—H molecules to become Si—OH molecules, and causes the Si—C chemical bond to disappear. In this example determining the extent of oxidation may comprise determining the amount of Si—H and Si—OH bonds in a sample, and/or determining the amount of S—C chemical bonds in a sample.

The method may be used, for example, in checking the condition of a photoconductor member and/or in deciding whether to clean the surface of a photoconductor member.

Figure 2:
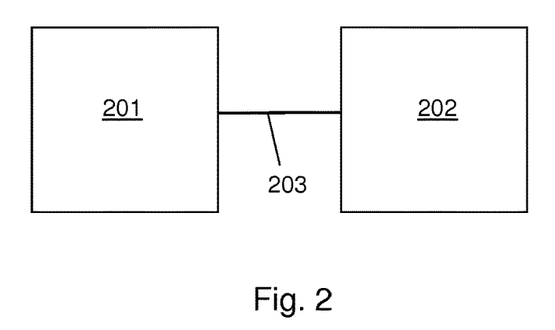
FIG. 2 is a simplified schematic of an example of apparatus for determining an extent of oxidation of a surface of a photoconductor member.

FIG. 2 shows an example of an apparatus suitable for use in performing the method of FIG. 1. The apparatus comprises an optical spectrometer 201. In some examples the optical spectrometer 201 is a FTIR spectrometer. In some examples the optical spectrometer 201 is a Raman spectrometer. The apparatus also comprises a processing unit 202 to receive a spectrum of a surface of a photoconductor member obtained by the optical spectrometer 201 and to determine an extent of oxidation of the surface based on the received spectrum. In the example of FIG. 2, the processing unit 202 is shown as being separate from the optical spectrometer 201. In some examples the processing unit 202 may be integrated into the optical spectrometer 201. The processing unit 202 is in electronic communication, e.g. by means of a wired or wireless communications link 203, with the optical spectrometer 201. In some examples the processing unit is to determine an extent of oxidation by detecting peaks corresponding to an oxidation product of a material comprised in the photoconductor member 201 in the received spectrum. In some examples the processing unit is to measure the height of detected peaks in the received spectrum. In some examples the processing unit is to compare the measured height of detected peaks in the received spectrum to a look-up table relating oxidation product peak height to extent of oxidation of the surface.

Figure 3:
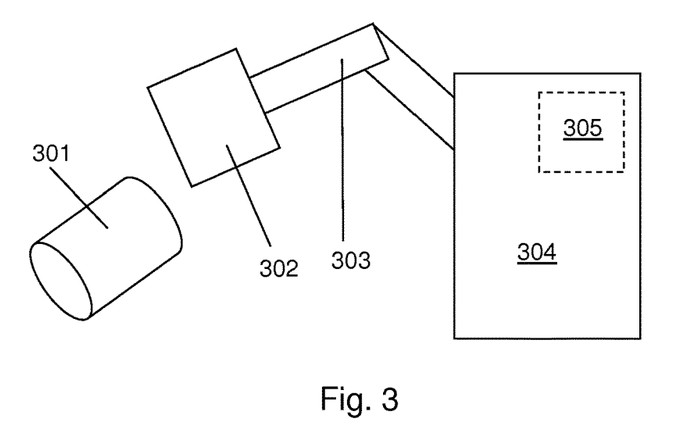
FIG. 3 is a simplified schematic of an example of apparatus for determining an extent of oxidation of a surface of a photoconductor member.

FIG. 3 shows an example of an apparatus suitable for use in performing the method of FIG. 1. The apparatus comprises an optical spectrometer 304. In some examples the optical spectrometer 304 is a FTIR spectrometer. In some examples the optical spectrometer 304 is a Raman spectrometer. The optical spectrometer 304 comprises a sample analysis compartment (not shown). An articulated arm 303 is mounted into the sample analysis compartment. In some examples the articulated arm 303 is a robotic arm. A measuring unit, e.g. a crystal, a tip, or simply a contact area, 302 is mounted on the distal end of the articulated arm 303. In some examples the measuring unit 302 is rotatably mounted such that it is rotatable around at least one axis with respect to the distal end of the articulated arm 303. In some examples the measuring unit 302 is a mercury cadmium telluride, MCT, detector. In some examples the measuring unit 302 is a deuterated triglycine sulphate, DTGS, detector. In some examples an attenuated total reflection, ATR, accessory is also mounted on the distal end of the articulated arm 303. In some examples the ATR accessory is to contact a crystal with the photoconductor member surface for which the spectrum is being obtained. In some such examples the ATR accessory comprises a silicon crystal. In some examples the ATR accessory comprises a germanium or zinc selenide crystal. The articulated arm 303 provides an optical path between the device or devices mounted on its distal end and the sample analysis compartment of the optical spectrometer 304.

The apparatus also comprises a processing unit 305 to receive a spectrum of a surface of a photoconductor member 301 obtained by the optical spectrometer 304 and to determine an extent of oxidation of the surface based on the received spectrum. In the example of FIG. 3, the processing unit 305 is integrated into the optical spectrometer 304. In some examples the processing unit 305 is to perform the determination in the same manner as the processing unit 202 described in relation to FIG. 2.

Figure 4:
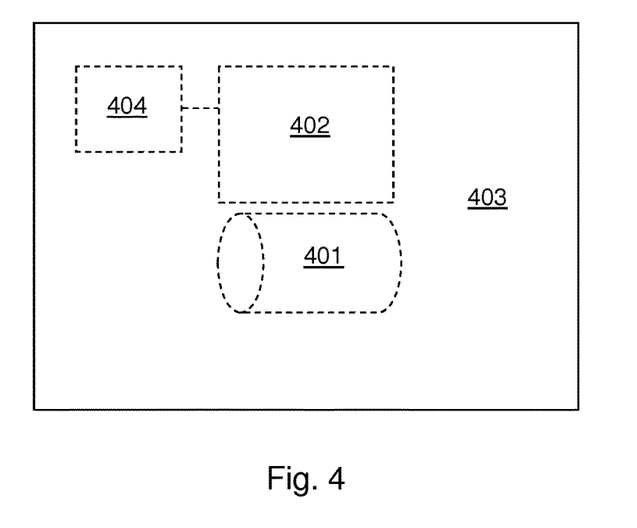
FIG. 4 is a simplified schematic of an example of apparatus for determining an extent of oxidation of a surface of a photoconductor member in-situ.

FIG. 4 shows an example of an apparatus suitable for use in performing the method of FIG. 1. The apparatus comprises an optical spectrometer 402. The optical spectrometer is integrated into a printing apparatus 403. The printing apparatus comprises a photoconductor member 401. The optical spectrometer 402 is positioned adjacent to the photoconductor member 401, so that the optical spectrometer 402 is able to obtain a spectrum of the surface of the photoconductor member 401. An optical path is provided between the surface of the photoconductor member 401 and a detector of the optical spectrometer 402, e.g. by means of fibre optic cables or mirrors. In some examples the optical spectrometer 402 is an FTIR spectrometer. In some examples the optical spectrometer 402 is a Raman spectrometer.

The optical spectrometer is in electronic communication with a processing unit 404. In the example of FIG. 4, the processing unit 404 is a processing unit of the printing apparatus 403. The processing unit 404 is to receive a spectrum of a surface of a photoconductor member 401 obtained by the optical spectrometer 402 and to determine an extent of oxidation of the surface based on the received spectrum. In some examples the processing unit 405 is to perform the determination in the same manner as the processing unit 202 described in relation to FIG. 2. In some examples the processing unit is additionally to control the operation of the printing apparatus 403. In some such examples the processing unit 404 is to selectively operate the printing apparatus 403 in a printing mode, in which the printing apparatus generates printed materials, or in a photoconductor analysis mode, in which the printing apparatus does not generate printed materials and in which the optical spectrometer 402 determines the extent of oxidation of a surface of the photoconductor member 401.

The example of FIG. 4 enables the in-situ determination of an extent of oxidation of the surface of a photoconductor member. In other words, the example of FIG. 4 enables an extent of oxidation of the surface of a photoconductor member to be determined whilst the photoconductor member is installed in a printing apparatus. The example therefore enables the down-time of the printing apparatus during determination of the extent of oxidation of the surface of a photoconductor member to be minimized.

Figure 5:
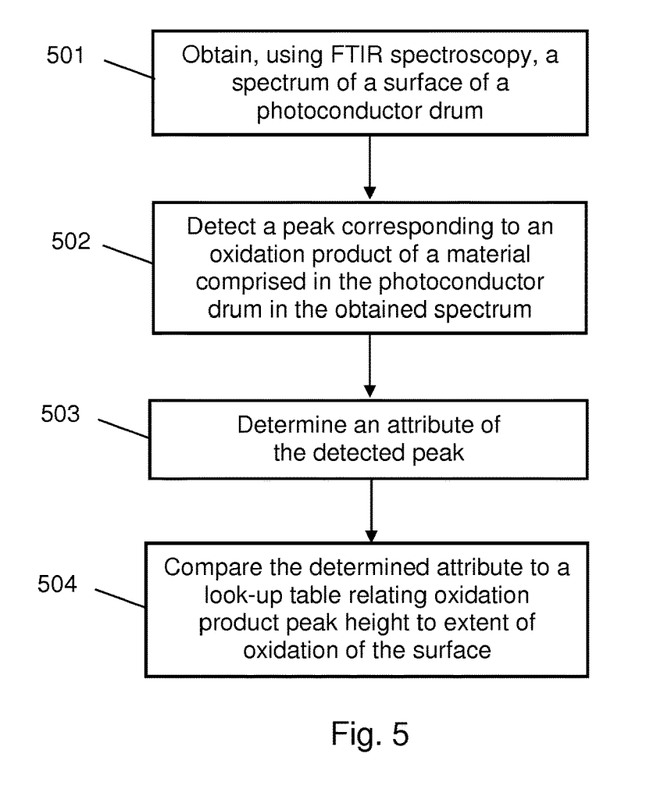
FIG. 5 is a flowchart of an example of a method of determining an extent of oxidation of a surface of a photoconductor member using FTIR spectroscopy.

FIG. 5 shows an example of a method. The method comprises obtaining, using FTIR spectroscopy, a spectrum of a surface of a photoconductor member, block 501. In some examples an ATR technique is used to obtain the spectrum. In some examples the photoconductor member is removed from a printing apparatus before block 501 is performed. In some examples block 501 is performed whilst the photoconductor member is installed in a printing apparatus.

Figure 6:
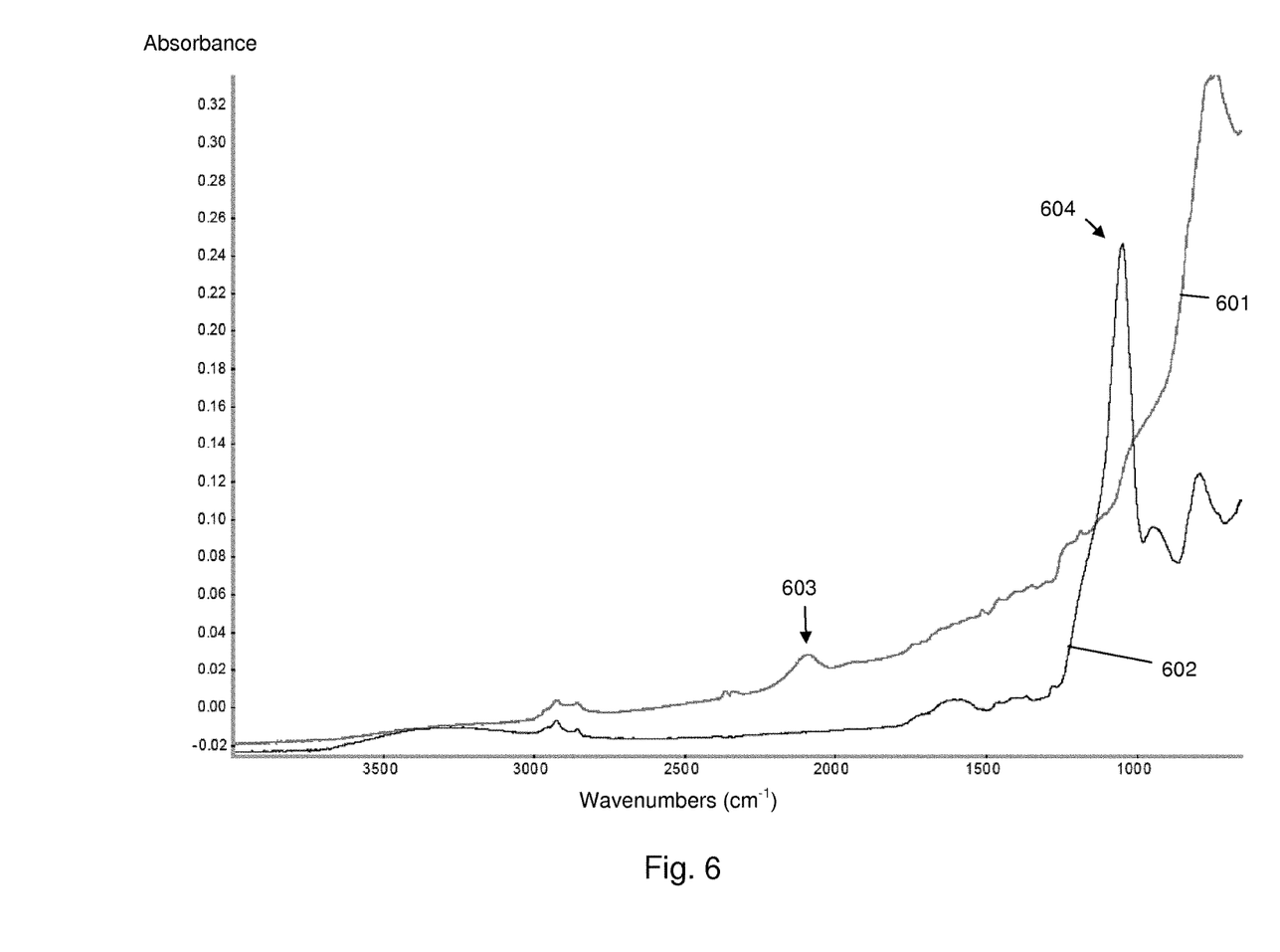
FIG. 6 show example FTIR spectra of photoconductor drum surfaces.

FIG. 6 shows example FTIR spectra obtained for new and used amorphous silicon photoconductor drums. The top signal 601 was obtained for a new photoconductor drum which had not yet been used in a printing apparatus. The bottom signal 602 was obtained for a used photoconductor drum which had experienced 7 million charging cycles. It can be seen that the signal 601 for the new photoconductor drum exhibits a peak 603 at 2090 cm$^{-1}$, corresponding to the Si—H bond, which is characteristic of hydrogenated amorphous silicon. By contrast the signal 602 for the used photoconductor drum does not exhibit a peak at this location but instead exhibits a peak 504 at 1040 cm$^{-1}$. This peak 604 corresponds to the Si—OH bond, which is characteristic of an oxidation product of silicon. Other peaks which may be present in a FTIR spectrum for an amorphous silicon photoconductor member and which can be used in a determination of the extent of oxidation of the member are:

1055-1060 cm$^{-1}$ (indicative of oxidation)
2100 cm$^{-1}$ (Si—H—indicative of a pristine member)
1350,1400,1450 cm$^{-1}$ (used for internal reference)
1740 cm$^{-1}$ (indicative of ink and/or oxidation on the member)
1245 cm-1 (Si—C)

1275 cm$^{-1}$ (Si—O$_3$)

1250-1500 cm$^{-1}$ (indicative of oxidation).

A detailed analysis of the signal 602 for the used photoconductor member can reveal the extent of oxidation, e.g. by revealing the amount of a certain type of bond in the measured sample.

In block 502 a peak corresponding to an oxidation product of a material comprised in the photoconductor member is detected in the obtained spectrum. In some examples in which the photoconductor member comprises amorphous silicon, a peak corresponding to the Si—OH bond, which occurs at 1040 cm$^{-1}$, is detected. It is intended that the term "detected" can encompass both positive and negative detections. A negative detection would occur, for example, if the method was performed on a photoconductor member which was not oxidised, meaning that the obtained spectra did not contain any peaks corresponding to oxidation products. In some examples more than one peak is detected in the obtained spectrum. In one example, a peak corresponding to the Si—OH bond is detected and a peak corresponding to the Si—C bond is detected.

In block 503 an attribute of the detected peak is determined. In some examples block 503 comprises measuring the height of the detected peak. In some examples block 503 comprises calculating the area under the detected peak. In some examples in which more than one peak has been detected, block 503 comprises measuring the height of and/or calculating the area under each detected peak. In some examples in which more than one peak has been detected, block 503 comprises determining a ratio of the heights and/or areas of two of the detected peaks. In cases where no peak has been detected, the outcome of block 503 is a value of zero.

The method also comprises, in block 504, comparing the determined attribute of the detected peak to a look-up table relating peak attribute value to extent of oxidation of the surface. In some examples the look-up table relates oxidation product peak height to extent of oxidation of the surface. In some examples the look-up table relates oxidation product peak area to extent of oxidation of the surface. It will be appreciated that the look-up table is specific to a particular photoconductor member material. A suitable look-up table may be created by obtaining spectra for photoconductor members of various usage levels, and then destructively analysing the same photoconductor members using a reference technique which permits the amount of oxidation to be determined quantitatively. EDS or XPS may be used for the quantitative analysis. The quantitative oxidation data can then be related to the oxidation product peak heights in a look-up table. In some examples a calibration graph or a correlation function relating oxidation product peak height to extent of oxidation is defined instead of or in addition to a look-up table. The extent of oxidation may be expressed in any of the forms described above in relation to block 102 of FIG. 2.

The examples enable an extent of the oxidation of a photoconductor member to be determined quantitatively. This in turn enables an accurate assessment to be made regarding whether the extent of the oxidation is sufficient to affect the print quality of documents printed using that photoconductor member.

Figure 7:
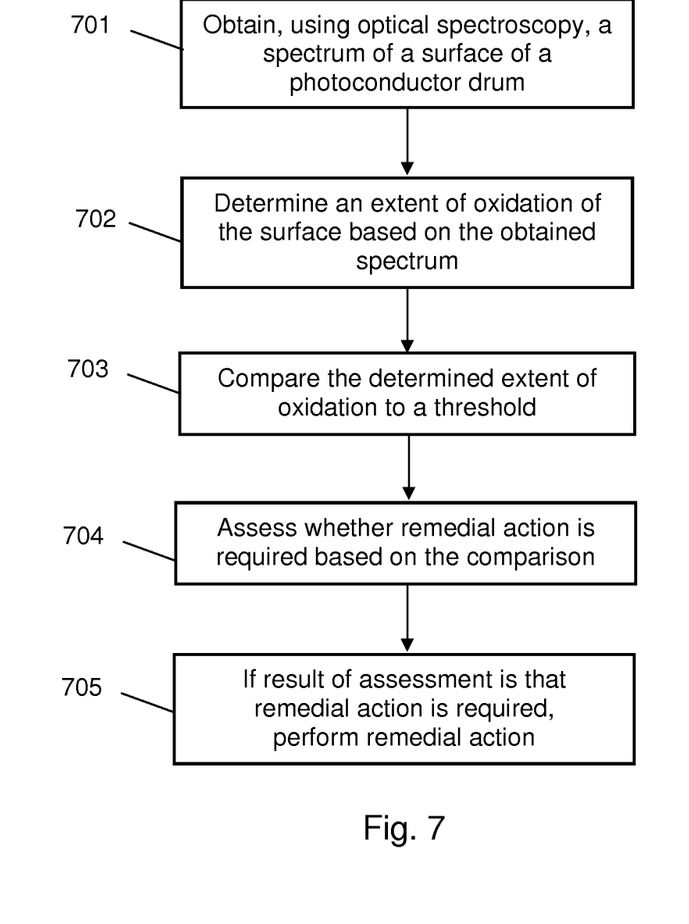
FIG. 7 is a flowchart of an example of a method of assessing whether to clean a surface of a photoconductor member.

FIG. 7 shows an example of a method of assessing whether to clean the surface of a photoconductor member. The method comprises obtaining, using optical spectroscopy, a spectrum of a surface of a photoconductor member, block 701. In block 702, an extent of oxidation of the surface is determined based on the obtained spectrum. In one example performing blocks 701 and 702 comprises performing blocks 101 and 102 of the method shown in FIG. 1. In one example performing blocks 701 and 702 comprises performing blocks 501 to 504 of the method shown in FIG. 5.

In block 703, the determined extent of oxidation of the surface of the photoconductor member is compared to a threshold. In some examples the threshold comprises a maximum numerical value for the amount of an oxidation product, or a component of an oxidation product, comprised in the photoconductor member. The determined extent of oxidation will be either less than, greater than, or equal to the threshold. In some examples block 703 comprises comparing the determined extent of oxidation of the surface of the photoconductor member to a first threshold and to a second, higher, threshold.

In block 704, whether remedial action is required is assessed based on the comparison. In some examples the remedial action comprises cleaning the surface of the photoconductor member and/or replacing the photoconductor member, i.e. in some examples block 704 comprises assessing whether to clean the surface of the photoconductor member, and/or assessing whether to replace the photoconductor member. In some examples a set of rules is defined, corresponding to the possible results of the comparison. In one example, if the extent of oxidation is less than or equal to the threshold, the result of the assessment is that remedial action is not required, and if the extent of oxidation is greater than the threshold, the result of the assessment is that remedial action is required. In one example, if the extent of oxidation is less than the threshold, the result of the assessment is that remedial action is not required, and if the extent of oxidation is greater than or equal to the threshold, the result of the assessment is that remedial action is required. In some examples in which the determined extent of oxidation of the surface of the photoconductor member has been compared to a first threshold and to a second threshold, if the extent of oxidation is less than the first threshold, the result of the assessment is that remedial action is not required, if the extent of oxidation is between the first threshold and the second threshold, the result of the assessment is that cleaning of the surface of the photoconductor member is to be performed, and if the extent of oxidation is greater than the second threshold, the result of the assessment is that the photoconductor member is to be replaced.

If the result of block 704 is that remedial action is required, at block 705 remedial action is performed. In some examples, if the result of the assessment is that cleaning is to be performed, block 704 comprises cleaning the surface of the photoconductor member to remove some or all of the oxidation. In some such examples the RCA procedure is used to clean the surface of the photoconductor member. In some examples cleaning of the photoconductor member is instigated automatically in response to an assessment that the cleaning is to be performed. In some examples, if the result of the assessment is that the photoconductor member is to be replaced, block 704 comprises replacement of the photoconductor member.

In some examples the method of FIG. 7 is performed periodically during the operational lifetime of a given photoconductor member.

Figure 8:
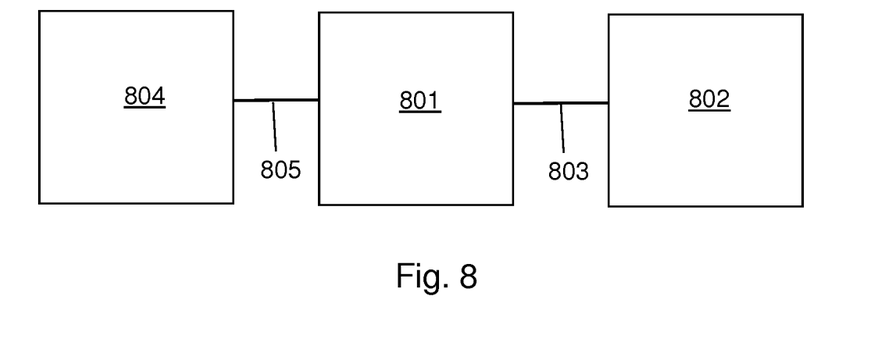
FIG. 8 is a simplified schematic of an example of apparatus for cleaning a photoconductor member.

FIG. 8 shows an example of an apparatus suitable for use in performing the method of FIG. 7. The apparatus comprises an optical spectrometer 801. In some examples the optical spectrometer 801 is the same as the optical spectrometer 201 described above in relation to FIG. 2. In some examples the optical spectrometer 801 is the same as the optical spectrometer 304 described above in relation to FIG. 3. In some examples the optical spectrometer 801 is the same as the optical spectrometer 402 described above in relation to FIG. 4. The apparatus also comprises a processing unit 802 to receive a spectrum of a surface of a photoconductor member obtained by the optical spectrometer 801 and to determine an extent of oxidation of the surface based on the received spectrum. The processing unit 802 is also to assess whether to clean the surface of the photoconductor member based on the determined extent of oxidation. In some examples the processing unit 802 is also to assess whether to replace the photoconductor member based on the determined extent of oxidation. The apparatus also comprises a cleaning apparatus 804 to remove an oxidation product from the surface of a photoconductor member. In some examples the cleaning apparatus 804 is to perform the RCA process. In some such examples the cleaning apparatus is to immerse the photoconductor member in a plurality of chemical solutions, e.g. an ammonia-hydrogen peroxide mixed solution, a hydrochloric acid-hydrogen peroxide mixed solution, a dilute hydrofluoric acid solution. In some such examples the cleaning apparatus is to rinse and dry the photoconductor member.

The processing unit 802 is in electronic communication, e.g. by means of a wired or wireless communications link 803, with the optical spectrometer 801. The processing unit 802 is also in electronic communication, e.g. by means of a wired or wireless communications link 805, with the cleaning apparatus 804. In some examples the processing unit is to cause the cleaning apparatus 804 to perform a cleaning process on a photoconductor member in dependence on the result of an assessment performed by the processing unit of whether the surface of the photoconductor member is to be cleaned. In some examples the apparatus shown in FIG. 8 is integrated into a printing apparatus.

The examples enable the operational lifetime of a photoconductor member to be significantly extended.

Examples in the present disclosure can be provided as methods, systems or machine readable instructions, such as any combination of software, hardware, firmware or the like. Such machine readable instructions may be included on a computer readable storage medium (including but is not limited to disc storage, CD-ROM, optical storage, etc.) having computer readable program codes therein or thereon.

The present disclosure is described with reference to flow charts and/or block diagrams of the method, devices and systems according to examples of the present disclosure. Although the flow diagrams described above show a specific order of execution, the order of execution may differ from that which is depicted. Blocks described in relation to one flow chart may be combined with those of another flow chart.

It shall be understood that each flow and/or block in the flow charts and/or block diagrams, as well as combinations of the flows and/or diagrams in the flow charts and/or block diagrams can be realized by machine readable instructions.

The machine readable instructions may, for example, be executed by a general purpose computer, a special purpose computer, an embedded processor or processors of other programmable data processing devices to realize the functions described in the description and diagrams. In particular, a processor or processing apparatus may execute the machine readable instructions. Thus functional modules of the apparatus and devices may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine readable instructions may also be stored in a computer readable storage that can guide the computer or other programmable data processing devices to operate in a specific mode.

Such machine readable instructions may also be loaded onto a computer or other programmable data processing devices, so that the computer or other programmable data processing devices perform a series of operation steps to produce computer-implemented processing, thus the instructions executed on the computer or other programmable devices provide a step for realizing functions specified by flow(s) in the flow charts and/or block(s) in the block diagrams.

Further, the teachings herein may be implemented in the form of a computer software product, the computer software product being stored in a storage medium and comprising a plurality of instructions for making a computer device implement the methods recited in the examples of the present disclosure.

While the method, apparatus and related aspects have been described with reference to certain examples, various modifications, changes, omissions, and substitutions can be made without departing from the spirit of the present disclosure. It is intended, therefore, that the method, apparatus and related aspects be limited only by the scope of the following claims and their equivalents. It should be noted that the above-mentioned examples illustrate rather than limit what is described herein, and that those skilled in the art will be able to design many alternative implementations without departing from the scope of the appended claims.

The word "comprising" does not exclude the presence of elements other than those listed in a claim, "a" or "an" does not exclude a plurality, and a single processor or other unit may fulfil the functions of several units recited in the claims.

The features of any dependent claim may be combined with the features of any of the independent claims or other dependent claims.

The invention claimed is:

1. A method comprising:
    obtaining, using optical spectroscopy, a spectrum of a surface of a photoconductor member; and
    determining an extent of oxidation of the surface based on the obtained spectrum.

2. A method as claimed in claim 1 wherein the obtaining step comprises using Fourier Transform Infrared, FTIR, spectroscopy to obtain the spectrum.

3. A method as claimed in claim 1 wherein the obtaining step comprises using Raman spectroscopy to obtain the spectrum.

4. A method as claimed in claim 1 wherein the determining step comprises detecting a peak corresponding to an oxidation product of a material comprised in the photoconductor member in the obtained spectrum and determining an attribute of the detected peak,
    wherein the determined attribute of the detected peak comprises one of: peak height, peak area, ratio of detected peak height with the height of a further peak in the obtained spectrum, ratio of detected peak area with an area of a further peak in the obtained spectrum.

5. A method as claimed in claim 4 wherein the determining step comprises comparing the determined attribute to a look-up table relating oxidation product attribute value to extent of oxidation of the surface.

6. A method as claimed in claim 1 comprising assessing whether remedial action is required based on the determined extent of oxidation,
wherein the remedial action comprises cleaning the surface of the photoconductor member and/or replacing the photoconductor member.

7. A method as claimed in 6 wherein the assessing step comprises comparing the determined extent of oxidation to a threshold, and wherein assessing whether to clean the surface of the photoconductor member is based on the comparison.

8. A method as claimed in claim 1 wherein the obtaining step is performed on a photoconductor member which is separate from a printing apparatus.

9. A method as claimed in claim 1 wherein the photoconductor member is in a printing apparatus during the obtaining step.

10. An apparatus comprising:
an optical spectrometer to obtain a spectrum of a surface of a photoconductor member; and
a processing unit to:
receive a spectrum obtained by the optical spectrometer; and
determine an extent of oxidation of the surface based on the received spectrum.

11. An apparatus as claimed in claim 10 wherein the optical spectrometer comprises an articulated arm mounted to a sample compartment of the optical spectrometer and a measuring unit mounted on the articulated arm, such that the articulated arm provides an optical path between the measuring unit and the sample compartment.

12. An apparatus as claimed in claim 11 wherein the optical spectrometer is to obtain a spectrum using attenuated total reflection, ATR.

13. An apparatus as claimed in claim 10 comprising a cleaning apparatus to remove an oxidation product from the surface of the photoconductor member.

14. A printing apparatus comprising the apparatus as claimed in claim 10.

15. A non-transitory machine-readable storage medium encoded with instructions executable by a processor, the machine-readable storage medium comprising:
instructions to detect receipt by the processor of a spectrum of a surface of a photoconductor member obtained using optical spectroscopy; and
instructions to determine an extent of oxidation of the surface of the photoconductor member based on the received spectrum.

* * * * *

UNITED STATES PATENT AND TRADEMARK OFFICE
CERTIFICATE OF CORRECTION

PATENT NO. : 10,215,711 B2
APPLICATION NO. : 15/521813
DATED : February 26, 2019
INVENTOR(S) : Eviatar Golan et al.

Page 1 of 1

It is certified that error appears in the above-identified patent and that said Letters Patent is hereby corrected as shown below:

In the Claims

In Column 9, Line 7, in Claim 7, after "in" insert -- claim --.

Signed and Sealed this
Second Day of July, 2019

Andrei Iancu
*Director of the United States Patent and Trademark Office*